US010575796B2

(12) United States Patent
Nayak et al.

(10) Patent No.: US 10,575,796 B2
(45) Date of Patent: Mar. 3, 2020

(54) COMPUTED TOMOGRAPHY GANTRY (71) Applicant: General Electric Company, Schenectady, NY (US)

(72) Inventors: Vishwanath Nayak, Bangalore (IN); Dhaval Dangashiya, Bangalore (IN)

(73) Assignee: General Electric Company, Schenectady, NY (US)

( * ) Notice: Subject to any disclaimer, the term of this patent is extended or adjusted under 35 U.S.C. 154(b) by 221 days.

(21) Appl. No.: 15/608,193

(22) Filed: May 30, 2017

(65) Prior Publication Data

US 2018/0344263 A1 Dec. 6, 2018

(51) Int. Cl.
*A61B 6/03* (2006.01)
(52) U.S. Cl.
CPC .................. *A61B 6/035* (2013.01)
(58) Field of Classification Search
CPC .. A61B 6/00; A61B 6/03; A61B 6/032; A61B 6/4007; A61B 6/4014; A61B 6/4447; A61B 6/035; A61B 6/44; A61B 6/4411; A61B 6/4429; A61B 6/4435; G01N 23/04; G01N 23/046; G01D 5/347; G01D 5/3473

USPC .......................................... 378/4, 15
See application file for complete search history.

(56) References Cited

U.S. PATENT DOCUMENTS

| | | | |
|---|---|---|---|
| 7,447,294 B2* | 11/2008 | Sadotomo | A61B 6/035 378/15 |
| 7,889,837 B2* | 2/2011 | Takamatsu | A61B 6/4488 378/19 |
| 2012/0241393 A1* | 9/2012 | Roth | A61B 6/035 211/26 |
| 2015/0030136 A1* | 1/2015 | Dodge | H05G 1/02 378/204 |

* cited by examiner

*Primary Examiner* — Jurie Yun
(74) *Attorney, Agent, or Firm* — McCoy Russell LLP (57) ABSTRACT A computed tomography (CT) gantry including a rotary base may be provided, having two faces opposite each other along a rotation axis of the rotary base. One of the two faces is to support each of a plurality of rotary computed tomography components. The plurality of rotary computed tomography components is to perform computed tomography imaging on a user.

20 Claims, 9 Drawing Sheets

COMPUTED TOMOGRAPHY GANTRY

TECHNICAL FIELD

Embodiments generally relate to a computed tomography (CT) gantry including a rotary base.

BACKGROUND

The CT gantry may be a mechanical base which may include a rotary base to hold and axially rotate imaging chain components around a patient. For example, the imaging chain components may include an X-ray tube, collimator, a detector to detect X-rays emitted by the X-ray tube, a generator, and power supply components. The imaging chain components may be disposed around a patient anatomy to produce continuous X-rays and to generate CT images from the X-rays. The CT gantry is subjected to high centrifugal forces and the factor of safety needed for structural components in the CT gantry is high to avoid harming the patient. Furthermore, vibration and deflection of the CT gantry may need to be contained within specific limits to ensure that image quality is not compromised.

DRAWINGS

The various advantages of embodiments will become apparent to one skilled in the art by reading the following specification and appended claims, and by referencing the following drawings, in which:

DESCRIPTION

Figure 1:
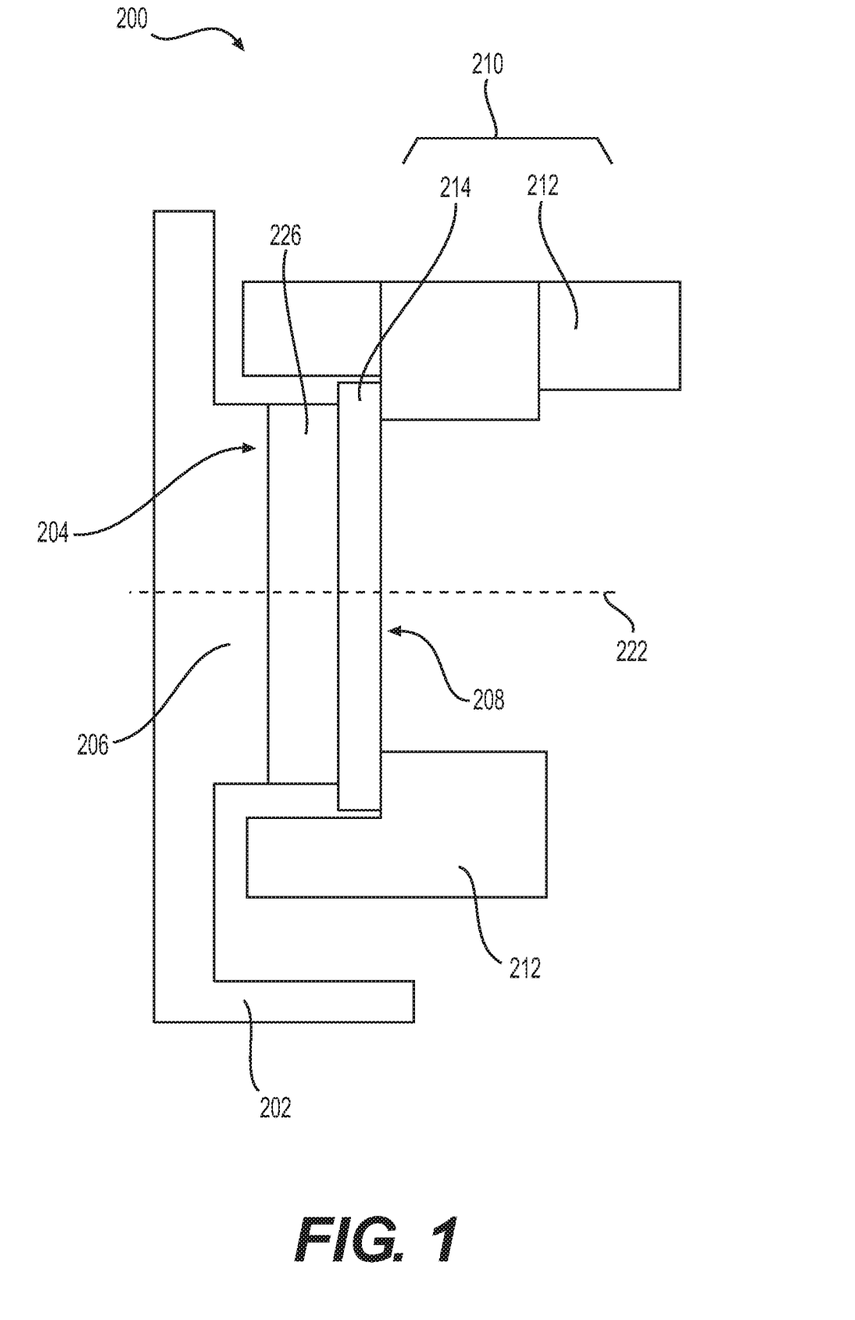
FIG. 1 illustrates a cross-sectional view of a CT gantry, in accordance with embodiments.

As illustrated in FIG. 1, a CT gantry 200 in accordance with embodiments is provided. In FIG. 1, a cross-sectional view of the CT gantry 200 is illustrated. The CT gantry 200 includes a stationary gantry base 202 having a protrusion 206 including a mounting surface 204. The CT gantry 200 further includes a rotary portion 210 being disposed so that the mounting surface 204 is received within a space of the rotary portion 210. The CT gantry 200 further includes a bearing 226 to support the rotary portion 210 and mounted to the mounting surface 204. Although the illustrated bearing 226 is substantially cylindrical in shape, cross-section, etc., embodiments are not limited thereto. For example, bearing 226 may encompass any shape, cross-section, etc. that permits practice of embodiments. The rotary portion 210 may include a rotary base 214 and a plurality of rotary CT components 212 mounted to a front face 208 of the rotary base 214. The front face 208 of the rotary base 214 may be opposite, along a rotation axis 222, from a back face of the rotary base 214 which is attached to the bearing 226. The plurality of rotary CT components 212 may be free of direct contact from outer peripheral side faces (e.g., upper and lower faces) of the rotary base 214.

In some embodiments, the plurality of rotary CT components 212 may be free of direct contact with every other face of the rotary base 214 except the front face 208. The rotary base 214 may have a uniform thickness and a curvilinear shape, cross-section, etc. The rotary base 214 may be unitary. The rotary portion 210 may rotate about the rotation axis 222 during operation to obtain a CT image of a patient. For example, each of the rotary base 214 and the plurality of rotary CT components 212 may rotate about the rotation axis 222 to obtain the CT scan. The bearing 226 may include a rotatable portion attached to the rotary base 214, and a stationary part attached to the mounting surface 204.

The rotary base 214 may carry and rotate heavy parts, such as the plurality of rotary CT components 212. The rotary base 214 may transfer a centrifugal load to the bearing 226, and the bearing 226 in turn may transfer the load to the stationary gantry base 202. The shape, size, configuration, etc. of the rotary base 214 may be modified to more uniformly distribute and reduce centrifugal forces transmitted to the bearing 226. For example, the curvilinear shape of the rotary base 214 is to result in a reduction of forces transmitted to the bearing 226. Furthermore, the rotary base 214 may have a rectangular cross-section or shape. A reduction in such forces may increase the quality of CT scans of a user.

In accordance with embodiments, the rotary base 214 may have a reduced thickness, for example, when compared to those of other designs. This is to reduce overall manufacturing costs.

Moreover, the rotary base 214 may have a uniform thickness along the rotation axis 222 which facilitates production as well providing a uniform distribution of forces to the bearing 226. The rotary CT components 212 may be stably attached to the front face 208, rather than outer circumferential side surfaces (e.g., upper surfaces and lower surfaces) of the rotary base 214 to allow for a better distribution of forces. For example, the rotary CT components 212 may be directly attached to the front face 208 rather than upper surfaces and lower surfaces of the rotary base 214.

As noted herein, the rotary base 214 may be unitary, and therefore, the entire rotary base 214 may uniformly support all of the rotary CT components 212. Furthermore, the rotary base 214 may have the rotary CT components 212 mounted to the front face 208, and may not require apertures on the side faces (e.g., top and bottom faces) of the rotary base 214 to allow the rotary CT components 212 to operate. The rotary base 214 may have a completely flat surface of the front face 208 upon which each of the rotary CT components 212 is to be mounted. Moreover, the rotary base 214 may include at least one of ribs and stiffeners.

In accordance with embodiments, the rotary base 214 may have a compact length. The length may be measured along the rotation axis 222 of the rotary base 214. This length may be referred to as the thickness of the rotary base 214. The thickness of the rotary base 214 may be 10-50 mm as measured along the rotation axis 222. In some embodiments, the thickness of the rotary base 214 may be 20-30 mm as measured along the rotation axis 222.

Figure 2A:
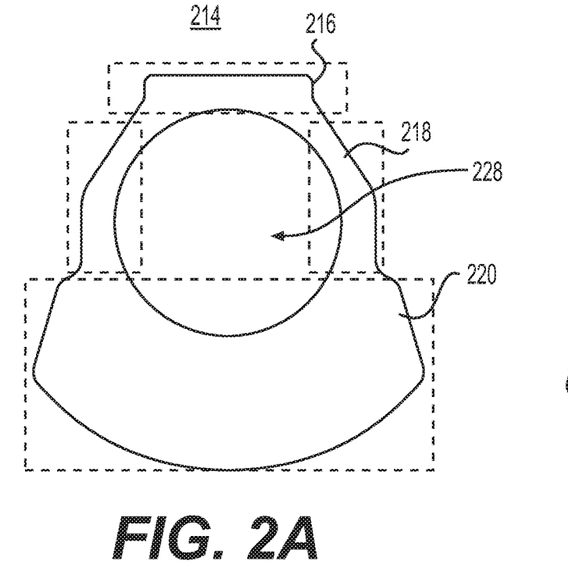
FIGS. 2A-2C illustrate rotary bases in accordance with embodiments.

As illustrated in FIG. 2A, the rotary base 214 may have a central hole 228. A patient may be disposed in the hole 228 to perform the CT imaging. An opening of the central hole 228 may have a predetermined diameter, such as, for example, of about 710 mm. A radius of the bottom surface 224, as measured from a center of the central hole 228 may have a predetermined value, such as, for example, of about 775 mm.

Figure 2B:
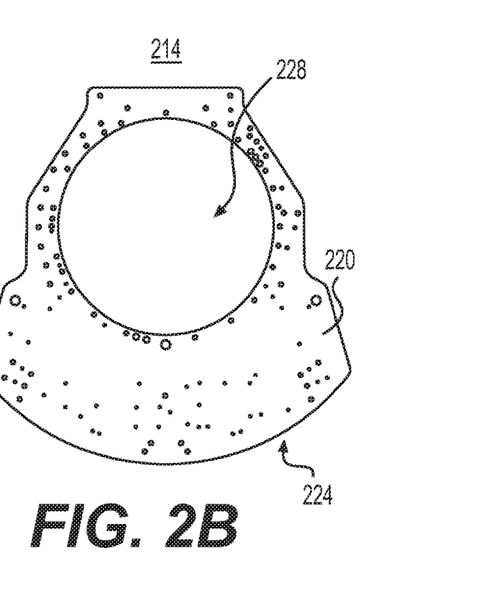

As illustrated in FIG. 2B, the rotary base 214 may have a maximum predetermined width of about 1220 mm, and a maximum predetermined height of about 1,233 mm. In some embodiments, the height may range from 1,233-1,500 mm. A predetermined distance measured between an uppermost part of the rotary base 214 to the center of the central hole 228 may be about 458 mm. A predetermined distance measured between the center of the central hole 228 to the bottommost part of rotary base 214, may be about 775 mm. In accordance with embodiments, the bottommost part of the rotary base 214 may comprise, for example, the bottom surface 224.

As noted, the rotary base 214 may also be curvilinear shaped. The curved bottom surface 224 may extend for an entire longest width of the rotary base 214, and may have a substantially uniform radius of curvature throughout. The radius may be measured from the center of the central hole 228 to the bottom surface 224. By forming the bottom surface 224, the rotary base 214 may increase the overall area of the bottom section 220, as illustrated in FIG. 2A. A larger bottom section 220 allows for various implementations of the rotary CT components 212. For example, different sizes, types, models, configurations, etc. of detectors may be placed in the bottom section 220, and at various locations. Moreover, the larger bottom section 220 provides a greater overall mass, which means that less counter weight blocks must be placed on the bottom section 220 to counter the weights of heavier components of the rotary CT components 212, which are mounted at a top of the rotary base 214.

By reducing the overall mass of the counter weight blocks, it is determined that forces, which are detrimentally formed during rotation of the rotary base 214 and the rotary CT components 212, are reduced or otherwise minimized. That is, by not having or reducing counter weight blocks, a more uniform distribution of weight may be achieved and a reduction of pushing and pulling forces. For example, the geometry of the curvilinear shaped design may enhance a distribution of bearing forces to be distributed uniformly both in radial and axial directions when the rotary CT components 212 are mounted on the rotary base 214. Therefore, the forces are uniformly distributed to the bearing 226 from the rotary base 214, and the bearing 226 may stiffen so that forces are more uniformly distributed.

In accordance with embodiments, the rotary base 214 may comprise steel or a compound of material components that includes steel. The steel, for example, may be International Standard 2062. In some embodiments, the rotary base 214 may be composed of only steel. In some embodiments, the rotary base 214 may be composed solely of International Standard 2062 steel. In some embodiments, the rotary base 214 may also comprise aluminum. In some embodiments, the rotary base 214 may be composed only of aluminum.

During operation of the CT gantry 200, the rotary base 214 and the rotary CT components 212 may rotate around a patient. A clearance (e.g., 12 mm) may need to be maintained between the rotary CT components 212 and the stationary gantry base 202 at top and bottom portions of the stationary gantry base 202. To provide such a clearance, the stationary gantry base 202 may include the protrusion 206. The mounting surface 204 may be a surface of the protrusion 206. The protrusion 206 may extend toward the rotary CT components 212, and have the mounting surface 204 formed at distal end thereof to be in a space formed by the rotary CT components 212 and be between the rotary CT components 212. The protrusion 206 may be between the rotary CT components 212 and in the space. The protrusion 206 may be cylindrical.

Figure 2C:
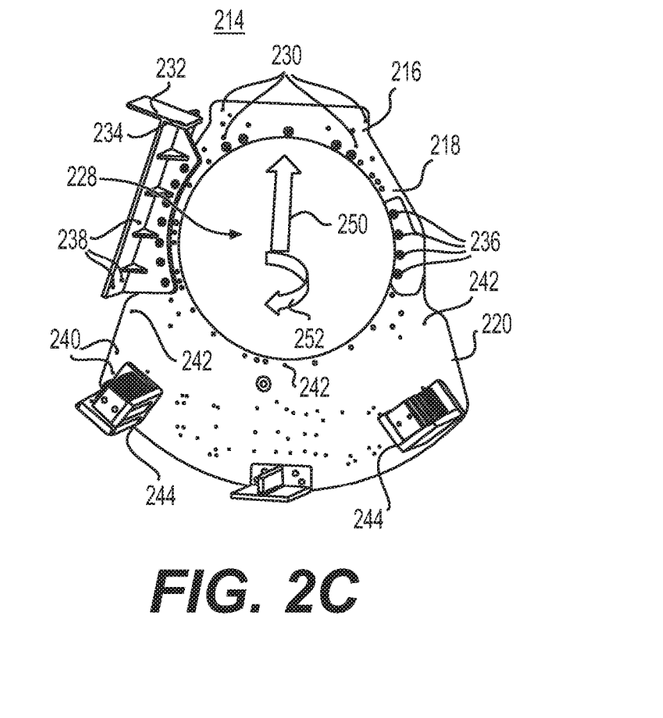

It may be less costly to manufacture the stationary gantry base 202 to have an increased size so that the protrusion 206 provides the clearance, rather than increasing the size of the rotary base 214 to provide the clearance. Therefore, the cost of the CT gantry 200 may be reduced. Furthermore, because the rotary base 214 is smaller, it may provide less force to the bearing 226 as the rotary base 214 rotates FIGS. 2A-2C illustrate embodiments of the rotary base 214. As illustrated, the rotary base 214 may be curvilinear shaped. In FIG. 2A, the rotary base 214 may include a top portion 216, a middle portion 218 and the bottom portion 220. The top portion 216 may support heavier ones of the rotary CT components 212. For example, the top portion may include an X-ray tube and collimator. The middle portion 218, which may also be referred to as a neck section, may support medium weighted ones of the rotary CT components 212. For example, the middle portion 218 may support a generator and power supply portions. The bottom section 220, which may also be referred to as a curvilinear bottom section, may support lighter ones of the rotary CT components 212, such as the detector, detector acquisition systems (DAS) boards, and balance blocks. The detector, X-ray tube and collimator may be collectively referred to as an "imager."

FIG. 2B further illustrates the rotary base 214 having various apertures. These apertures are sized and disposed to be compatible with numerous CT architectures, and may therefore be used in various designs.

FIG. 2C illustrates the rotary base 214 in further detail, and an example of various mounting positions of the rotary CT components 212. The rotary base 214 may include mounting positions 230-242, each of which may have mounted thereupon at least one of the rotary CT components 212. Mounting positions 230, 232, 234 may be within top portion 216. The mounting position 230 may be to mount thereupon a collimator and an X-ray tube assembly. The mounting position 232 may be to mount thereupon a power module and a fuse box assembly. The mounting position 234 may be to mount thereupon an auxiliary power module.

Mounting positions 236 and 238 are within middle portion 218. Mounting position 236 may be to mount thereupon a generator. Mounting position 238 may be to mount thereupon power supply components Mounting positions 240 and 242 may be within the bottom portion 220. Mounting position 240 may be to mount thereupon power supply components. Mounting position 242 may be to mount thereupon a detector. Balance blocks 244 are not required in some embodiments, but may optionally be attached to the rotary base 214.

As illustrated in FIG. 2C, the rotary base 214 may be subjected to a gravitational acceleration (i.e., 9.81 m/s$^2$) in a direction toward the mounting position 230 and along arrow 250. The rotary base 214 may also have an inertia force along arrow 252 due to rotation.

The bottom section 220 may also have a curvilinear shaped section, and may be designed in such a way to balance the heavy overall mass of the X-ray tube, and the collimator. For example, the profile of the rotary base 214 may be wider at the bottom section 220 to accommodate the DET geometry, and may also be spread and curved out uniformly at the bottom portion to balance uniformly. For example, balance blocks 244 may not required to be mounted upon the rotary base 214 to balance the X-ray tube and the collimator. Moreover, by having a uniform thickness, cantilever forces on the bearing 226 and stationary gantry base 202 may be reduced. This allows for a reduction in weight of the CT gantry 200, and allows the CT gantry 200 to become more cost effective and lighter. Furthermore, the rotary base 214 may allow for 0.5 sec/revolution.

Moreover, the design of the curvilinear shaped rotary base 214 may reduce mass and inertia, resulting in a lighter gantry design. For example, a neck length, i.e., the length of the middle portion 218, may have a reduced overall length to allow for surface contact of the rotary CT components 212 mounting and safe bolt engagement.

Figure 3A:
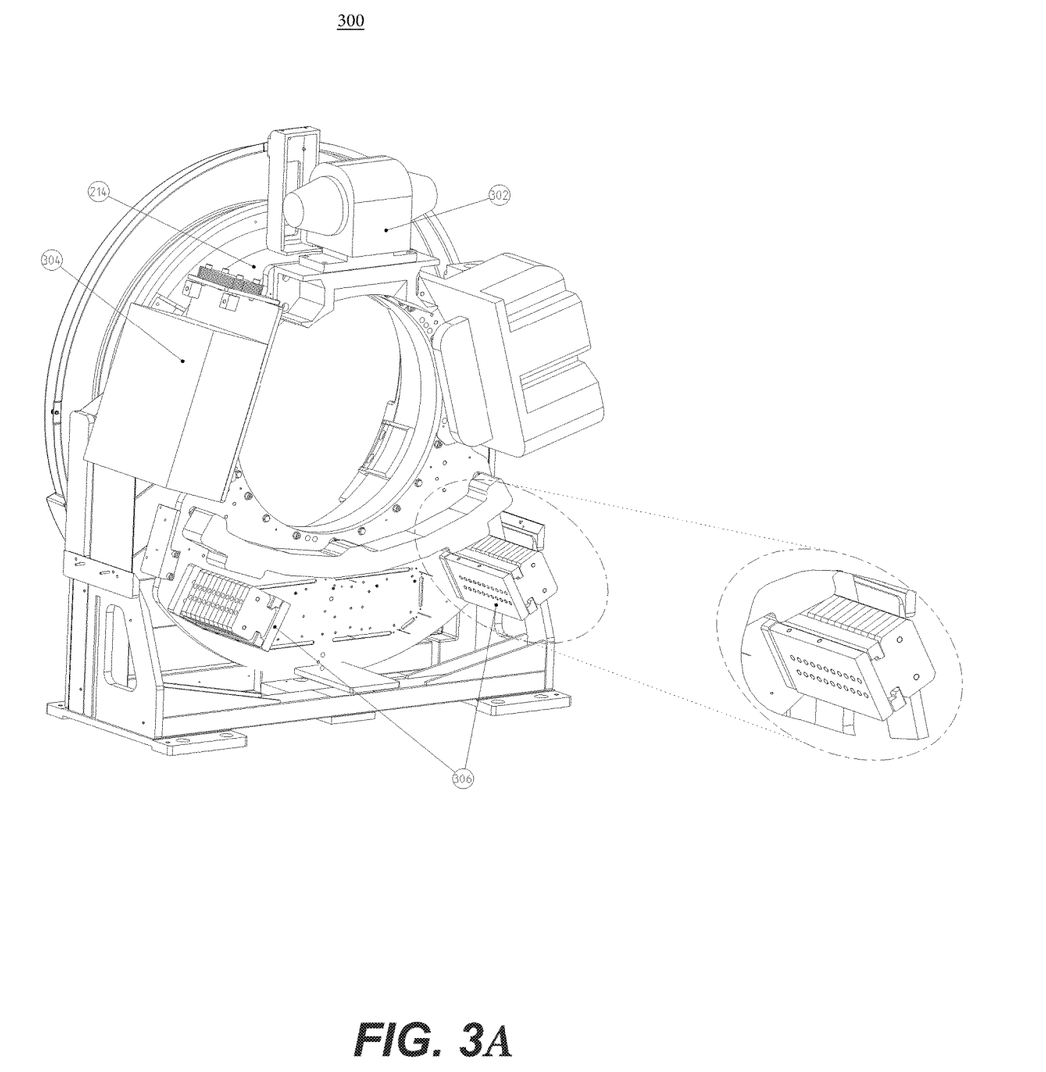
FIG. 3A illustrates a CT gantry, in accordance with embodiments.
Figure 3B:
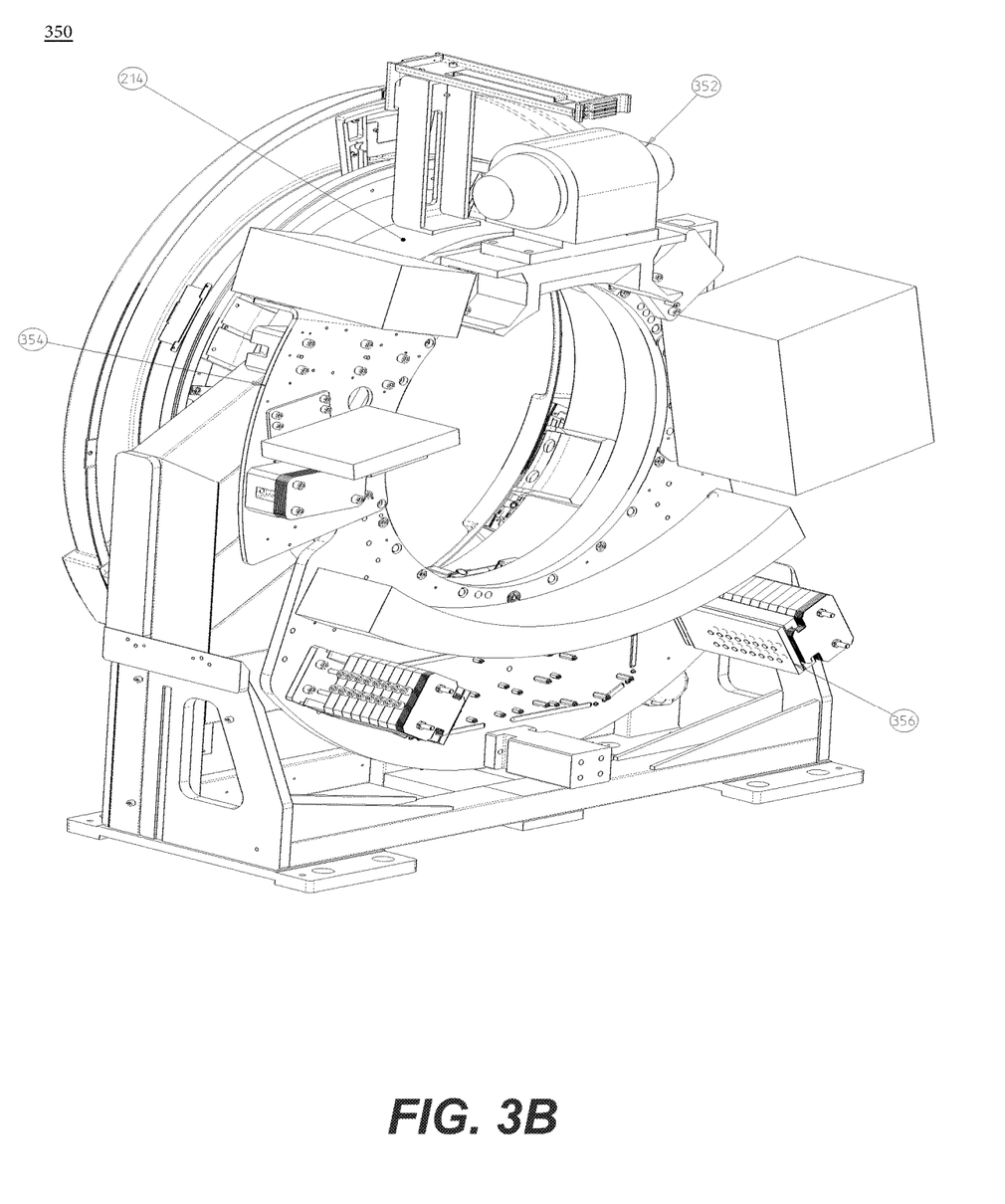
FIG. 3B illustrates a CT gantry, in accordance with embodiments.

FIGS. 3A-3B illustrate two different CT gantries 300 and 350, each of which includes the rotary base 214. The CT gantries 300, 350 include similar elements as the CT gantry 200, with some modifications as discussed below.

As illustrated in FIG. 3A, the CT gantry 300 includes the rotary base 214. The rotary base 214 supports a first product configuration, in which a total rotating mass is about 550 Kg. The speed may be about 0.5 second/revolution. The rotating gantry envelope may be about 1570 mm. High capacity and heavier X-ray tube 302, and generator 304 may be mounted on the CT gantry 300. Balance blocks 306 may also be mounted to the rotary base 214.

As illustrated in FIG. 3B, a CT gantry 350 includes the rotary base 214 as illustrated and described herein. In accordance with embodiments, the overall rotating mass of the CT gantry 350 may be around 390 Kg. The total speed of the CT gantry 350 may be around 1 second/revolution. The rotating gantry envelope may be around 1490 mm. The CT gantry 350 may have a low capacity, lighter X-ray tube 352, and lighter generator 354 compared respectively to the high capacity and heavier X-ray tube 302, and heavier generator 304. The CT gantry 350 may experience lower centrifugal forces than the CT gantry 300. A balance block 356 may also be mounted to the rotary base 214.

In accordance with embodiments, the balance block 306 may have a less overall weight compared to the balance block 356, to thereby provide for better balancing to compensate the high mass of the X-ray tube 302 and collimator thereof. In contrast, the balance block 356 may have a greater overall weight than balance block 306, to thereby provide for balancing of the lighter X-ray tube 352 and collimator combination. The CT gantry 300 may be subject to higher centrifugal and gravitational loads than the CT gantry 350.

Thus, the rotary base 214 in accordance with embodiments is to be adaptable and scalable to various product designs. For example, the curvilinear shaped, unitary rotary base 214 may enable configurable with different gantry architectures with different combinations of balance and design. That is, the rotary base 214 has several provisions for accommodating multiple product configurations to accommodate different imagers (e.g., tubes and detector) and generators.

Figure 4:
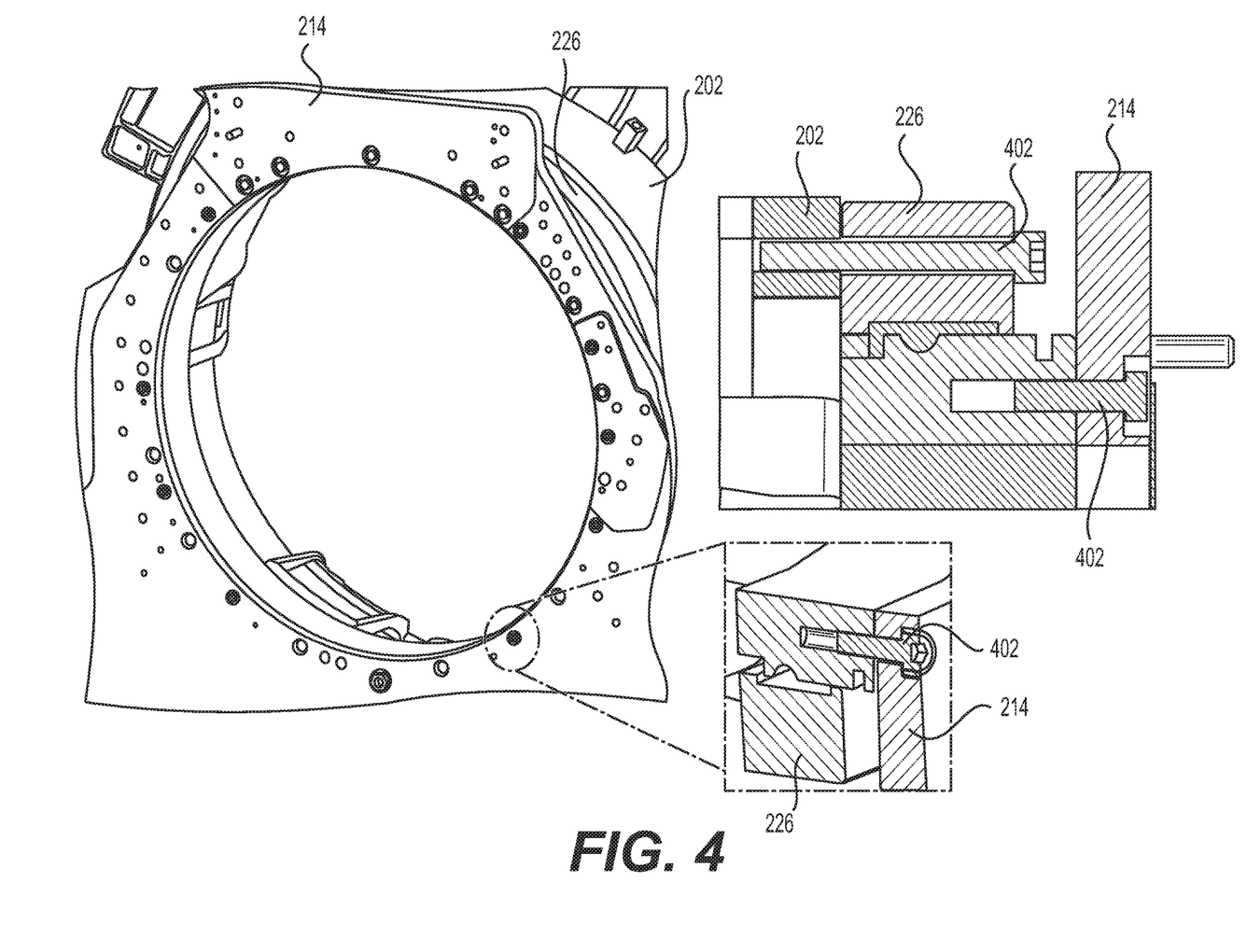
FIG. 4 illustrates a CT gantry, in accordance with embodiments.

FIG. 4 illustrates several close-up views of the CT gantry 200. The bearing 226 has a first bolt 402 to couple the bearing 226 to the stationary gantry base 202, which may be the protrusion 206. Furthermore, the bearing 226 has a second bolt 402 to couple the bearing 226 to the rotary base 214.

Figure 5:
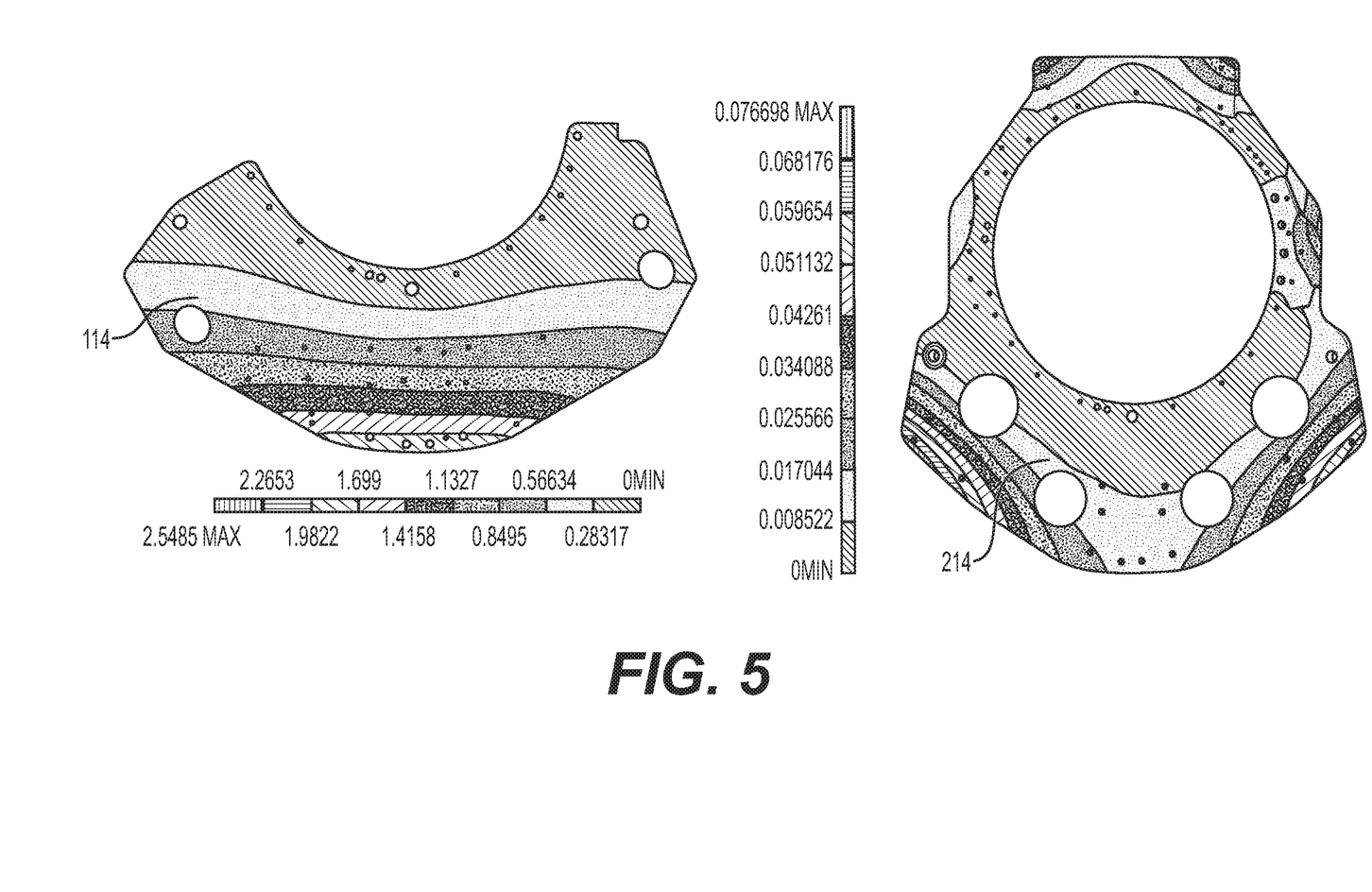
FIG. 5 illustrates a deflection map of rotary bases.

FIG. 5 illustrates data describing some advantages of the rotary base 214 compared to another design 114, and graphs the test result comparison. FIG. 5 provides a maximum deflection map with measurements being in millimeters. The maximum deflection with a 370 kg mass may be around 2.2 mm for the rotary base 114 at around 0.8 sec/revolution or 75 rpm. In contrast, the rotary base 214 may have a maximum deflection of around 0.08 mm at 460 kg at 0.5 seconds at 120 RPM.

Figure 6A:
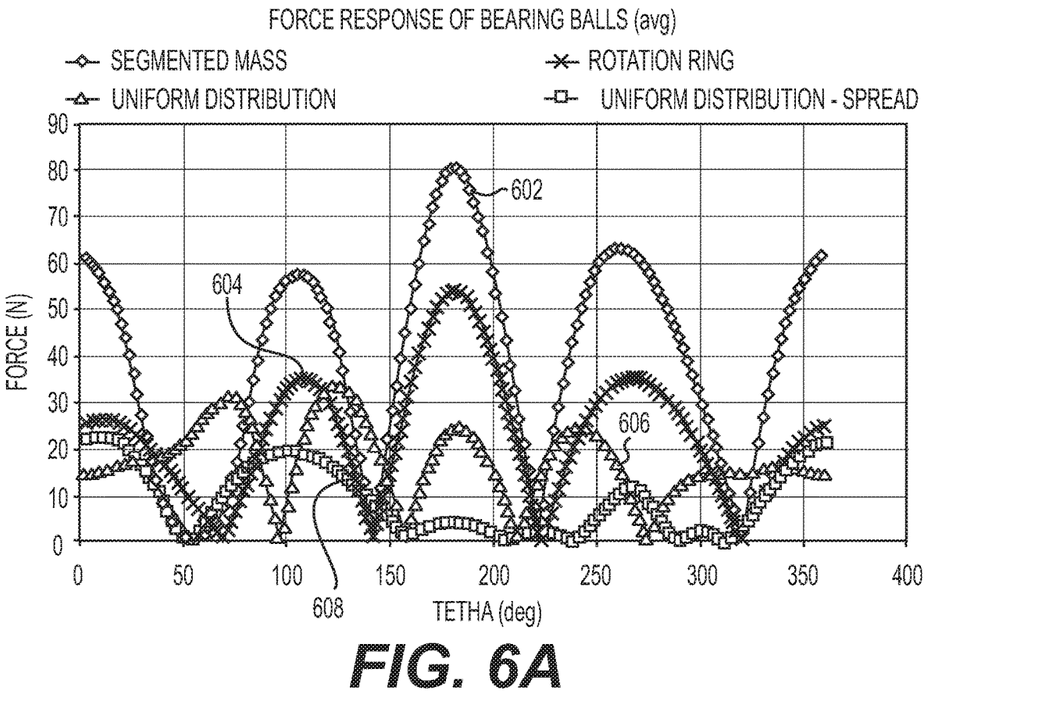
FIG. 6A illustrates a force response of CT gantries.
Figure 6B:
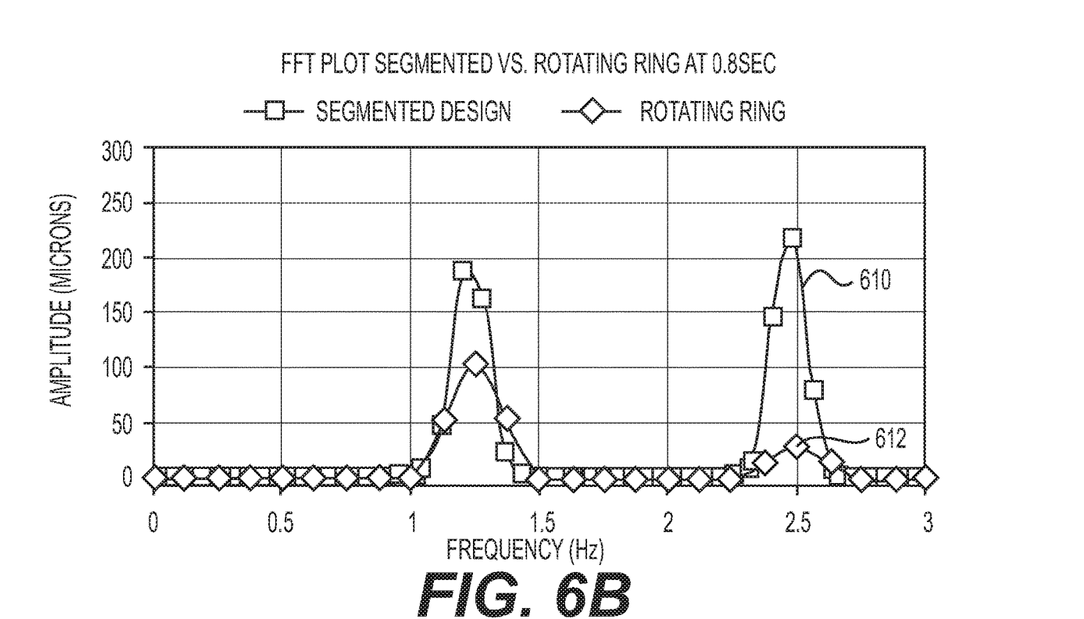
FIG. 6B illustrates deflection of CT gantries.

FIGS. 6A-6B illustrate data describing some advantages of the rotary base 214 compared to other designs, and graphs the test result comparison.

FIG. 6A illustrates the forces 608 along 360 degrees position of the rotary base 214 during operation, and forces 602, 604, 606 of various other tested models. The force is measured in a direction perpendicular to a rotation direction of the rotary base being tested. For example, if the rotary base rotates in the X-Y plane, the force would be measured along the Z-axis.

The X-ray tube may be at the 12 o'clock position (i.e., 0 deg) in each of the designs. The bearing forces are a representation of deflection of the rotary bases of the tested models and are proportional to gantry motion. As the bearing forces lower and become more uniform, less deflection and motion will occur in the respective CT Gantry of the rotary bases.

In detail, the forces 602 are greatest at 80 Newtons (N). Notably, the curvilinear shaped, unitary rotary base 214 produces the least maximum force 608 at 20 Newtons.

FIG. 6B illustrates the second harmonic amplitude (i.e., motion) of deflection 610 at different frequencies of a rotary base versus the amplitude of deflection 612 at different frequencies of the curvilinear, uniform thickness, unitary rotary base 214. As noted, the deflection 610 is substantially higher, around 220 microns, compared to the deflection 612 at 30 microns. The measured deflection is illustrated in FIG. 6B as the "amplitude." The deflection 612 of the rotary base 214 is less than the deflection 610 of another rotary base.

The lowered deflection 612 and lowered force 608 may be in part because the rotary base 214 may have all the mass of the rotary CT components 212 on a single plate of the rotary base 214. This will distribute the forces uniformly, and hence the CT gantry 200 capabilities may be increased to allow for a higher mass and higher speed to carry higher G-forces. The curvilinear-shaped design of the rotary base 214 has a better structural integrity which may increase an overall factor of safety and lessens deflection of the CT gantry 200, the rotary base 214 and mounting parts of the rotary base 214.

The rotary base 214 may also be balanced. For example, the rotary base 214 may be symmetrical in geometry, and may have an inherent mass at the bottom of the curvilinear configuration, which counters the heavy mass of the X-ray tube and collimator which may be located at a top of the rotary base 214 or at 12 o'clock position. Therefore, static and dynamic balancing may be performed more easily. Furthermore, the rotary base 214 may be lighter, and require less power to rotate.

Figure 7:
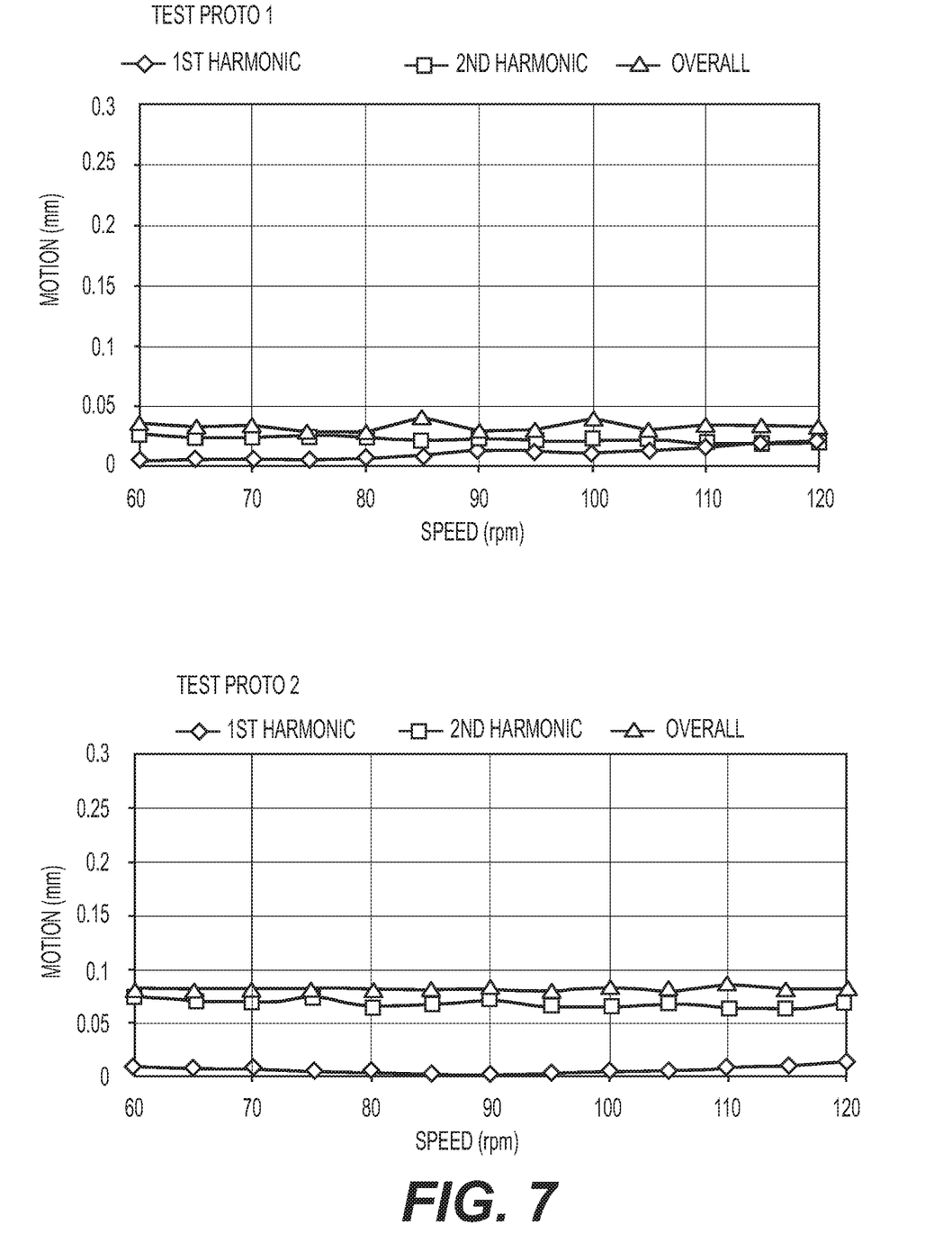
FIG. 7 illustrates motion of CT gantries in accordance with embodiments.

FIG. 7 illustrates motion data from two different simulations from the CT gantry 200, which includes the rotary base 214, that was built with heavy masses. As illustrated, in both simulations the gantry motion is well below CT specifications for motion, and is better than other deflection motion designs. For example, the deflection of the rotary base 214 concept was measured to check the Gantry motion and deflection. The measured Gantry motion and vibration values were ⅕th of the CT Gantry specification, which was derived from the allowable image quality requirements for better performance. FIG. 7 may show that the rotary base 214 have enhanced force response and the bearing deflection.

Figure 8:
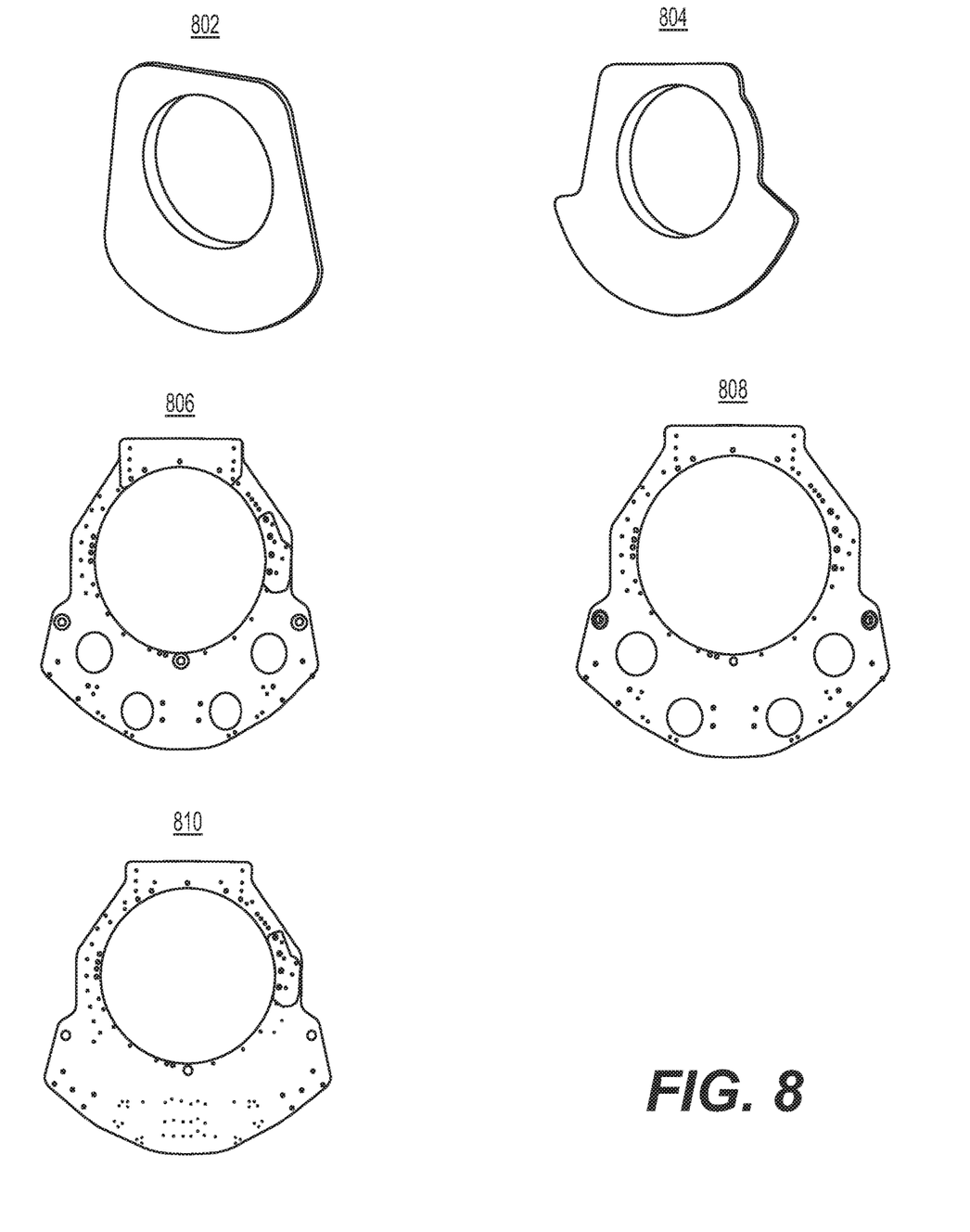
FIG. 8 illustrates rotary bases in accordance with embodiments.

FIG. 8 illustrates several rotary bases 802, 804, 806, 808, 810 which are variations of the rotary base 214. The rotary bases 802, 804, 806, 808, 810 may be included in the CT gantry 200 in place of the rotary base 214. The rotary bases 802, 804, 806, 808, 810 may include different shapes and apertures for mounting the rotary CT components 212.

The rotary bases 214, 802, 804, 806, 808, 810 described above may be made from a single plate manufacturing process could or casting material of a pre-fabricated plate.

ADDITIONAL NOTES AND EXAMPLES

Example 1 may include a gantry, comprising: a stationary gantry base having a protrusion including a mounting surface; a rotary portion defining a space to receive the mounting surface; and a bearing to support the rotary portion and to be mounted to the mounting surface.

Example 2 may include the gantry of Example 1, wherein the rotary portion includes a rotary base to be attached to the bearing.

Example 3 may include the gantry of Example 2, wherein the rotary base includes two faces opposite each other along a rotation axis of the rotary portion.

Example 4 may include the gantry of Example 2, wherein the rotary base is unitary.

Example 5 may include the gantry of Example 2, wherein the rotary base has a completely flat surface.

Example 6 may include the gantry of Example 2, wherein the rotary base has a curved bottom surface.

Example 7 may include the gantry of Example 6, wherein the curved bottom surface extends for an entire width of the rotary base.

Example 8 may include the gantry of Example 6, wherein the width is in a direction perpendicular to a rotation axis of the rotary portion.

Example 9 may include the gantry of Example 2, wherein the rotary base is formed to uniformly distribute forces to the bearing.

Example 10 may include the gantry of Example 2, wherein the rotary base has a uniform thickness as measured along a rotation axis of the rotary portion.

Example 11 may include the gantry of Example 2, wherein the rotary base includes at least one material selected from the group consisting of steel and aluminum.

Example 12 may include an apparatus, comprising: a rotary base having two faces opposite each other along a rotation axis of the rotary base, one of the two faces to support each of a plurality of rotary computed tomography components, the plurality of rotary computed tomography components to perform computed tomography imaging on a user.

Example 13 may include the apparatus of Example 12, wherein the rotary base is unitary.

Example 14 may include the apparatus of Example 12, wherein the rotary base has a curved bottom surface.

Example 15 may include the apparatus of Example 14, wherein the curved bottom surface extends for an entire width of the rotary base, the width being in a direction perpendicular to the rotation axis of the rotary base.

Example 16 may include the apparatus of Example 12, wherein the rotary base has a uniform thickness as measured along the rotation axis of the rotary base.

Example 17 may include the apparatus of Example 12, wherein the one face has a completely flat surface upon which each of the plurality of rotary computed tomography components is to be mounted.

Example 18 may include the apparatus of Example 12, wherein the rotary base includes at least one of ribs and stiffeners.

Example 19 may include the apparatus of Example 12, wherein the rotary base includes at least one material selected from the group consisting of steel and aluminum.

Example 20 may include the apparatus of Example 12, wherein the plurality of rotary computed tomography components is to be attached to the one face to be free of direct contact from every other face of the rotary base.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" or "at least one of" may mean any combination of the listed terms. For example, the phrases "one or more of A, B or C" may mean A; B; C; A and B; A and C; B and C; or A, B and C. In addition, a list of items joined by the term "and so forth", "and so on", or "etc." may mean any combination of the listed terms as well any combination with other terms.

Those skilled in the art will appreciate from the foregoing description that the broad techniques of the embodiments may be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

What is claimed is:

1. A gantry, comprising:
   a stationary gantry base having a protrusion including a mounting surface;
   a rotary portion defining a space to receive the mounting surface, wherein the rotary portion comprises tomography components on a first face; and
   a bearing to support the rotary portion and to be mounted to the mounting surface;
   wherein the protrusion extends into a space formed between the tomography components.

2. The gantry of claim 1, wherein the rotary portion includes a rotary base to be attached to the bearing.

3. The gantry of claim 2, wherein the rotary base includes two faces opposite each other along a rotation axis of the rotary portion.

4. The gantry of claim 2, wherein the rotary base is unitary.

5. The gantry of claim 2, wherein the rotary base has a completely flat surface.

6. The gantry of claim 2, wherein the rotary base has a curved bottom surface.

7. The gantry of claim 6, wherein the curved bottom surface forms a continuous curve for an entire width of the rotary base.

8. The gantry of claim 7, wherein the width is in a direction perpendicular to a rotation axis of the rotary portion.

9. The gantry of claim 2, wherein the rotary base is to uniformly distribute forces to the bearing.

10. The gantry of claim 2, wherein the rotary base has a uniform thickness as measured along a rotation axis of the rotary portion.

11. The gantry of claim 2, wherein the rotary base includes at least one material selected from the group consisting of steel and aluminum.

12. The gantry of claim 1, wherein a rotatable portion of the bearing is attached to the rotary portion.

13. The gantry of claim 12, wherein a stationary part of the bearing is attached to the mounting surface.

14. An apparatus, comprising:
   a rotary base having two faces opposite each other along a rotation axis of the rotary base, one face of the two faces to support each of a plurality of rotary computed tomography components, the plurality of rotary computed tomography components to perform computed tomography imaging on a user;
   wherein the rotary base has a bottom surface that forms a continuous curve for an entire width of the rotary base, the width being in a direction perpendicular to the rotation axis of the rotary base;
   wherein a bottom section of the rotary base is larger than a top section of the rotary base.

15. The apparatus of claim 14, wherein the rotary base is unitary.

16. The apparatus of claim 14, wherein the rotary base has a uniform thickness as measured along the rotation axis of the rotary base.

17. The apparatus of claim 14, wherein the one face has a completely flat surface upon which each of the plurality of rotary computed tomography components is to be mounted.

18. The apparatus of claim 14, wherein the rotary base includes at least one of ribs and stiffeners.

19. The apparatus of claim 14, wherein the rotary base includes at least one material selected from the group consisting of steel and aluminum.

20. The apparatus of claim 14, wherein the plurality of rotary computed tomography components is to be attached to the one face to be free of direct contact from every other face of the rotary base.

* * * * *